United States Patent [19]

Engelhardt et al.

[11] Patent Number: 4,853,415
[45] Date of Patent: * Aug. 1, 1989

[54] 2-(SUBSTITUTED SULFAMYL) DERIVATIVES OF 4-NITROBENZAMIDE AS RADIATION SENSITIZERS

[75] Inventors: Edward L. Engelhardt, Gwynedd Valley; Walfred S. Saari, Lansdale, both of Pa.

[73] Assignee: Merck & Co., Inc., Rahway, N.J.

[*] Notice: The portion of the term of this patent subsequent to Mar. 3, 2004 has been disclaimed.

[21] Appl. No.: 279,340

[22] Filed: Dec. 5, 1988

Related U.S. Application Data

[63] Continuation of Ser. No. 178,783, Mar. 30, 1988, abandoned, which is a continuation of Ser. No. 937,277, Dec. 3, 1986, abandoned.

[51] Int. Cl.$^4$ .................... A61K 31/18; C07C 143/78
[52] U.S. Cl. .................... 514/603; 514/183; 514/210; 514/331; 514/428; 546/233; 548/569; 548/950; 548/967; 564/87
[58] Field of Search .................. 564/87; 548/569, 950, 548/967; 546/233; 514/603, 331, 428, 210, 183

[56] References Cited

U.S. PATENT DOCUMENTS 4,603,133 7/1986 Engelhardt et al. ................ 514/229
4,647,588 3/1987 Engelhardt et al. ............. 564/87 X
4,731,369 3/1988 Engelhardt et al. ................ 514/327

OTHER PUBLICATIONS

Narayanan, V. L. et al., *Adv. Pharmacol. Chemother.*, 19, 174–175 (1982).
Halliwell, B. et al., *Free Radicals in Biology and Medicine*, Clarendon Press, Oxford, 1985, pp. 238–241.
Wardman, P., "Radiation Chemistry in the Clinic: Hypoxic Cell Radiosensitizers for Radiotherapy", manuscript to be published.

Primary Examiner—Richard A. Schwartz
Attorney, Agent, or Firm—Hesna J. Pfeiffer; Roy D. Meredith; Charles M. Caruso

[57] ABSTRACT 2-(Substituted sulfamyl) derivatives of 4-nitrobenzamide are disclosed as agents that increase the sensitivity of hypoxic cancer cells to x-rays and γ-radiation. Methods of preparing such compounds, protocols for administering them to human patients and animals, and pharmaceutical compositions containing them are also disclosed.

6 Claims, No Drawings

2-(SUBSTITUTED SULFAMYL) DERIVATIVES OF 4-NITROBENZAMIDE AS RADIATION SENSITIZERS

This is a continuation of application Ser. 178,783, filed 3-30-88 now abandoned, which is a continuation of application Ser. No. 937,277 filed 12-03-86, now abandoned.

BACKGROUND OF THE INVENTION

This application is related to U.S. Ser. No. 068,814, filed June 28, 1987, Merck Case 17308CA, which is a continuation of U.S. Ser. No. 795,567, filed Nov. 6, 1985, Merck Case 17308, now abandoned. This application is also related to U.S. Pat. No. 4,603,133.

The present disclosure encompasses novel and unobvious compounds useful for increasing the sensitivity of hypoxic cancer cells to x-rays and γ-radiation. The compounds of the present invention include 2-(substituted sulfamyl) derivatives of 4-nitro-benzamides, which, being weak bases, concentrate in tumors.

Certain compounds of the nitroimidazole group such as metronidazole and misonidazole, have been shown to have toxic side effects that limit their effectiveness as radiation sensitizers. The compounds of the present invention are effective radiation sensitizers and are believed to have a more favorable therapeutic ratio.

DETAILED DESCRIPTION OF THE INVENTION

The compositions of the present invention are 4-nitrobenzamides of the formula:

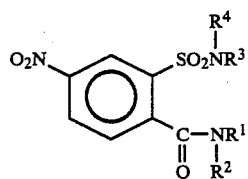

wherein:
R$^1$ is hydrogen or loweralkyl of 1–4 carbons;
R$^2$ and R$^4$ are the same or different and are each hydrogen, loweralkyl of 1–4 carbons, or hydroxyloweralkyl;
R$^3$ is loweralkyl of 1–4 carbons substituted with

wherein Q$^1$ is the same or different from Q$^2$ and both Q$^1$ and Q$^2$ are hydrogen, loweralkyl of 1–4 carbons, or hydroxyloweralkyl, or Q$^1$ and Q$^2$ taken together with the nitrogen atom in

form an heterocyclic ring such as aziridinyl, azetidinyl, pyrrolidinyl or piperidinyl; or physiologically acceptable salts thereof.

A variety of synthetic routes are available for compounds of Formula I. The 2-(substituted sulfamyl) derivatives of 4-nitrobenzoic acid, ester and amide compounds can be prepared by the following procedures.

Typically, a 4-nitroanthranilate ester is diazotized, then treated with sulfur dioxide and cupric chloride to yield a 2-chlorosulfonyl-4-nitrobenzoate intermediate. The sulfonyl chloride is dissolved in an aprotic solvent such as tetrahydrofuran, dioxane, dimethoxyethane, or chloroform and then treated with a quantity of an amine of the formula:

wherein the substituents R$^4$ and R$^3$ are defined above. Alternatively, other substituted nitrobenzoate esters or a nitrobenzamide having a 2-chlorosulfonyl substituent may be used as starting materials in the reaction with compounds of Formula II.

The reaction with compounds of formula II is preferably conducted in the presence of a base for neutralization of HCl. Such bases as tertiary amines, e.g. triethylamine, N,N-diisopropylethylamine, are useful for such neutralization. Alternatively, addition of a quantity of amine well in excess of equimolar amounts has a substantially similar effect. In this event, the reactant amine is utilized both to form the sulfonamide and to neutralize the HCl formed in the amination reaction. The reaction is preferably carried out at about 0°–25° C. for a period of up to 24 hours.

The product of the amination reaction is a compound of the formula:

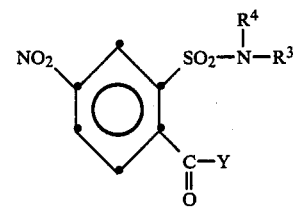

wherein Y is alkyloxy. If instead R$^4$=H, the product is frequently a benzisothiazol derivative of the formula:

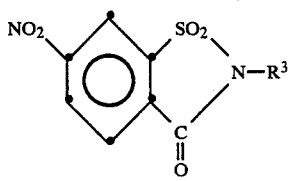

The final step in synthesis involves reaction of compounds of formula III or IV with the compound of the formula:

yielding benzamide derivatives as the products of the invention. The formation of such benzamides is typically carried out in polar solvents such as lower aliphatic alcohols, dimethylformamide, or dimethylsulfoxide. Other suitable solvents include tetrahydrofuran, glyme, diglyme, chloroform or methylene chloride. The reaction temperature is not critical, but the preferable range is 25°–50° C. for a period of up to 10 days. When low boiling amines are used, the reaction may be run in a sealed vessel.

The method of treatment of human patients or domestic animals undergoing radiation treatment of malignant disease processes employs the compounds of the present invention in parmaceutical compositions that are administered orally or parenterally. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between about 0.25 to about 4.0 grams per square meter of body surface.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for parenteral administration is a sterile isotonic solution of the drug. Oral dosage forms such as tablets, capsules, or elixirs may also be used.

Capsules or tablets containing 25, 50, 100 or 500 mg of drug/capsule or tablets are satisfactory for use in the method of treatment of our invention.

The following examples are intended to illustrate but do not limit the process of preparation, product, compositions, or method of treatment aspects of the invention. Temperatures are in degrees Celsius unless otherwise indicated throughout the application.

EXAMPLES

Ethyl 2-chlorosulfonyl-4-nitrobenzoate

A solution of sodium nitrite (19.6 g, 0.284 mol) in water (77 ml) was added slowly to a well stirred solution of ethyl 4-nitroanthranilate (55.6 g, 0.265 mol) in glacial acetic acid (300 ml) and concentrated hydrochloric acid (500 ml) cooled to $-5°$. After addition was complete, the mixture was stirred at $-5°$ to $0°$ for an additional 30 minutes and then added, in portions, to a cold solution of cupric chloride dihydrate (21.24 g) and sulfur dioxide (165 g) in glacial acetic acid (330 ml) and water (54 ml). The reaction mixture was stirred in an ice bath for 3 hours and then poured into ice. The precipitated light yellow solid was removed by filtration and dried to give the sulfonyl chloride (68.2 g, 87.6%), m.p. 66°–68°.

Anal. Calcd. for $C_9H_8ClNO_6S$: C, 36.81; H, 2.75; N, 4.77. Found: C, 37.06; H, 2.60; N, 4.80.

2-(2-Dimethylaminoethyl)-5-nitro-2H-1,2-benzoisothiazol-3-one, 1,1-Dioxide Hydrochloride A solution of N,N-dimethylethylenediamine (4.76 g, 54 mmol) and N,N-diisopropylethylamine (6.98 g, 54 mmol) in tetrahydrofuran (50 ml) was added over 35 minutes to a stirred, cooled solution of ethyl 2-chlorosulfonyl-4-nitrobenzoate (27.6 g, 94 mmol) in tetrahydrofuran (400 ml). After addition was complete, the reaction mixture was stirred in the ice bath for 1 hour, at 20°–25° for 20 hours and then concentrated under reduced pressure. After partitioning between ethyl acetate and water, the ethyl acetate extract was washed with a saturated sodium bicarbonate solution and a saturated solution of sodium chloride, dried ($Na_2SO_4$) and concentrated. The residue was treated with anhydrous ethanolic hydrogen chloride solution and recrystallized from MeOH-EtOAc-hexane to give the hydrochloride salt (9.23 g, 50.9%), m.p. 226°–27°.

Anal. Calcd. for $C_{11}H_{13}N_3O_5S \cdot HCl$: C, 39.35; H, 4.20; N, 12.51. Found: C, 39.66; H, 4.31; N, 12.52.

N,N-Dimethyl-2-[N-(2-dimethylaminoethyl)aminosulfonyl]-4-nitrobenzamide Hydrochloride 2-(2-Dimethylaminoethyl)-5-nitro-2H-1,2-benzisothiazol-3-one, 1,1-dioxide hydrochloride (7.09 g, 21.1 mmol) was added in portions to a cold solution of anhydrous dimethylamine (23.3 g, 0.52 mol) in methanol (170 ml). The solution was allowed to warm slowly to room temperature and was stirred at 20°–25° for 20 hours. After concentrating under reduced pressure, the residue was treated with anhydrous ethanolic hydrogen chloride solution and the resulting hydrochloride salt recrystallized from MeOH-EtOAc to give 6.87 g (85.4%) of product, m.p. 212°–14°.

Anal. Calcd. for $C_{13}H_{20}N_4O_5S \cdot HCl$: C, 41.00; H, 5.56; N, 14.71. Found: C, 41.36; H, 5.44; N, 14.96.

N-Ethyl-2-[N-(2-dimethylaminoethyl)aminosulfonyl]-4-nitrobenzamide Hydrochloride Hydrate A solution of ethylamine (13 ml, 0.20 mol) and 2-(2-dimethylaminoethyl)-5-nitro-2H-1,2-benzisothiazol-3-one, 1,1-dioxide hydrochloride (9.3 g, 27.7 mmol) in methanol (200 ml) was allowed to stand at 20°–25° for 18 hours. After concentrating under reduced pressure, the residue was flash chromatographed over silica gel and product eluted with 7% methanol-93% chloroform. The hydrochloride salt was prepared with anhydrous ethanolic hydrogen chloride and the salt recrystallized from MeOH-EtOAc-hexane to give 9.1 g (86.3%) of product, m.p. 97°–100°.

Anal. Calcd. for $C_{13}H_{20}N_4O_5S \cdot HCl \cdot H_2O$: C, 39.14; H, 5.81; N, 14.05. Found: C, 38.93; H, 5.74; N, 14.23.

N-(2-Hydroxyethyl)-2-[N-(2-dimethylaminoethyl)aminosulfonyl]-4-nitrobenzamide Hydrochloride Ethanolamine (12.1 ml, 0.20 mol) was added to a cold solution of 2-(2-dimethylaminoethyl)-5-nitro-2H-1,2-benzisothiazol-3-one, 1,1-dioxide hydrochloride (9.3 g, 27.7 mmol) in methanol (200 ml). After stirring at ice bath temperature for 2 hours, the reaction mixture was stirred at 20°–25° for 18 hours and then concentrated under reduced pressure. The residue was flash chromatographed over silica gel and product eluted with 15% methanol-85% chloroform. The hydrochloride salt was prepared with anhydrous ethanolic hydrogen chloride and the salt recrystallized from MeOH- EtOAc-hexane to give 10.1 g (91.9%) of product, m.p. 185° soften, 189°–190°.

Anal. Calcd. for $C_{13}H_{20}N_4O_6S \cdot HCl$: C, 39.34; H, 5.33; N, 14.12. Found: C, 39.54; H, 5.66; N, 14.28.

While the foregoing examples provide illustrations of the principles of the present invention, it will be readily understood that the practice, spirit and scope of the present invention encompasses other subject matter, as indicated in part by the appended claims.

What is claimed is:

1. A 2-(substituted sulfamyl) derivative of 4-nitrobenzamide, of the formula:

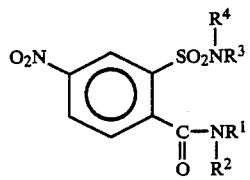

wherein:

$R^1$ is hydrogen or loweralkyl of 1–4 carbons;

$R^2$ and $R^4$ are the same or different and are each hydrogen, loweralkyl of 1–4 carbons, or hydroxyloweralkyl;

$R^3$ is loweralkyl of 1–4 carbons substituted with

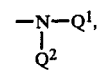

wherein $Q^1$ is the same or different from $Q^2$ and both $Q^1$ and $Q^2$ are hydrogen, loweralkyl of 1–4 carbons, or hydroxyloweralkyl, or $Q^1$ and $Q^2$ taken together with the nitrogen atom in

form an heterocyclic ring selected from aziridinyl, azetidinyl, pyrrolidinyl or piperidinyl; or any physiologically acceptable salt thereof.

2. N-N-Dimethyl-2-[N-(2-dimethylaminoethyl)-aminosulfonyl]-4-nitrobenzamide or a physiologically acceptable salt thereof.

3. N-Ethyl-2-[N-(2-dimethylaminoethyl)amino-sulfonyl]-4-nitrobenzamide or a physiologically acceptable salt thereof.

4. N-(2-Hydroxyethyl)-2-[N-(2-dimethylaminoethyl)aminosulfonyl]-4-nitrobenzamide or a physiologically acceptable salt thereof.

5. A pharmaceutical composition for enhancing the therapeutic effect of radiation which consists of an effective amount of a compound defined in claim 1 or 2 or 3 or 4, and a non-toxic pharmaceutically acceptable carrier.

6. A method for enhancing the therapeutic effect of radiation which comprises administering to a patient in need of such radiation treatment an effective amount of a compound defined in claim 1 or 2 or 3 or 4.

* * * * *